US00PP14727P2

(12) United States Plant Patent
Hofmann

(10) Patent No.: US PP14,727 P2
(45) Date of Patent: Apr. 20, 2004

(54) NEW GUINEA IMPATIENS PLANT NAMED 'FISUPNIC SALMON'

(50) Latin Name: *Impatiens hawkeri*
Varietal Denomination: Fisupnic Salmon

(76) Inventor: Birgit Christa Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 10/452,975

(22) Filed: Jun. 3, 2003

(51) Int. Cl.[7] ..... A01H 5/00

(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Fisupnic Salmon', characterized by its outwardly spreading and uniformly mounded plant habit; tall growth habit; freely branching and freely flowering habit; dark green-colored foliage; and large, nearly rounded, orange red-colored flowers that are positioned above and beyond the foliage.

1 Drawing Sheet

Botanical classification/cultivar designation: *Impatiens hawkeri* cultivar Fisupnic Salmon.

BACKGROUND OF THE INVENTION

The present Invention relates to a new and distinct cultivar of New Guinea Impatiens plant, botanically known as *Impatiens hawkeri,* and hereinafter referred to by the name 'Fisupnic Salmon'.

The new Impatiens is a product of a planned breeding program conducted by the Inventor in Hillscheid, Germany and Galder, Gran Canaria, Spain. The objective of the breeding program is to develop new vigorous Impatiens cultivars with medium flowering response and large rounded flowers with attractive coloration.

The new Impatiens originated from a cross-pollination made by the Inventor during the spring of 1999 of the *Impatiens hawkeri* cultivar Danharsal, disclosed in U.S. Plant Pat. No. 12,090, as the female, or seed, parent with the *Impatiens hawkeri* Kipas, disclosed in U.S. Plant Pat. No. 10,432, as the male, or pollen, parent. The cultivar Fisupnic Salmon was discovered and selected by the Inventor as a flowering plant within the progeny of the stated cross-pollination in a controlled environment in Galder, Gran Canaria, Spain in April, 2000.

Asexual reproduction of the new cultivar by terminal cuttings taken in Galder, Gran Canaria, Spain, since July, 2000, has shown that the unique features of this new Impatiens are stable and reproduced true to type in successive generations.

SUMMARY OF THE INVENTION

The following traits have been repeatedly observed and are determined to be the unique characteristics of 'Fisupnic Salmon'. These characteristics in combination distinguish 'Fisupnic Salmon' as a new and distinct Impatiens cultivar:

1. Outwardly spreading and uniformly mounded plant habit; tall growth habit.
2. Freely branching and freely flowering habit.
3. Dark green-colored foliage.

4. Large, nearly rounded, orange red-colored flowers that are positioned above or beyond the foliage.

Plants of the new Impatiens are most similar to plants of the female parent, the cultivar Danharsal. In side-by-side comparisons conducted by the Inventor in Hillscheid, Germany, plants of the new Impatiens differed from plants of the cultivar Danharsal in the following characteristics:

1. Plants of the new Impatiens were taller and more vigorous than plants of the cultivar Danharsal.
2. Plants of the new Impatiens had longer, narrower and lighter green-colored leaves than plants of the cultivar Danharsal.
3. Plants of the new Impatiens had larger flowers than plants of the cultivar Danharsal.
4. Plants of the new Impatiens had darker colored flowers than plants of the cultivar Danharsal.

Plants of the new Impatiens can be compared to plants of the male parent, the cultivar Kipas. In side-by-side comparisons conducted by the Inventor in Hillscheid, Germany, plants of the new Impatiens differed from plants of the cultivar Kipas in the following characteristics:

1. Plants of the new Impatiens were larger and more vigorous than plants of the cultivar Kipas.
2. Plants of the new Impatiens and the cultivar Kipas differed in flower coloration as plants of the cultivar Kipas had purple-colored flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Fisupnic Salmon' grown in a container.

DETAILED BOTANICAL DESCRIPTION

The cultivar Fisupnic Salmon has not been observed under all possible environmental conditions. The phenotype may vary somewhat with variations in environment such as temperature and light intensity, without, however, any variance in genotype.

The aforementioned photograph, following observations and measurements describe plants grown in Hillscheid, Germany, under commercial production practice in a glass-covered greenhouse. Rooted young plants were planted in 12-cm containers and the aforementioned photograph and following observations and measurements were taken about 11 weeks later. During the production of the plants, day temperatures were about 18 to 22° C. and night temperatures were about 16 to 18° C. In the following description, color references are made to The Royal Horticultural Society Colour Chart, 1995 Edition, except where general terms of ordinary dictionary significance are used.

Botanical classification: *Impatiens hawkeri* cultivar Fisupnic Salmon.

Parentage:

*Female parent.*—*Impatiens hawkeri* cultivar Danharsal, disclosed in U.S. Plant Pat. No. 12,090.

*Male parent.*—*Impatiens hawkeri* cultivar Kipas, disclosed in U.S. Plant Pat. No. 10,432.

Propagation:

*Type cutting.*—Terminal tip cuttings.

*Time to initiate roots.*—Summer: About 8 to 10 days at 24° C. Winter: About 12 to 15 days at 21° C.

*Time to produce a rooted cutting.*—Summer: About 15 days at 24° C. Winter: About 18 to 20 days at 21° C.

*Root description.*—Numerous, fibrous, and freely branching; 158D in color.

Plant description:

*General appearance.*—Outwardly spreading and uniformly mounded plant growth habit; tall growth habit; freely branching habit; bushy appearance; freely flowering. Vigorous.

*Crop time.*—From a rooted cutting, about 9 to 10 weeks are required to produce finished flowering plants in 12-cm containers.

*Plant height.*—About 26.5 cm.

*Plant diameter or spread.*—About 38 to 43 cm.

*Lateral branches.*—Quantity per plant: About 8 to 10. Length: About 22 to 24 cm. Diameter: About 7 to 8 mm. Internode length: About 4 to 6 cm. Texture: Smooth, glabrous. Color: 143B occasionally overlain with 180B.

*Foliage description.*—Arrangement: Primarily in whorls. Length: About 13 to 14 cm. Width: About 4 to 4.5 cm. Shape: Elliptic, narrow. Apex: Acuminate. Base: Acute. Margin: Serrulate with ciliation. Texture: Smooth, somewhat rugose; glabrous. Color: Developing foliage, upper surface: 139A. Developing foliage, lower surface: 185B to 185C. Fully expanded foliage, upper surface: 139A. Fully expanded foliage, lower surface: Light green 138A, and purple, 185C, marbled. Venation, upper surface: 53C. Venation, lower surface: 53D. Petiole: Length: About 1.5 to 2 cm. Diameter: About 3 mm. Texture: Smooth, glabrous. Color, upper surface: 53C. Color, lower surface: 53D.

Flower description:

*Flower type and flowering habit.*—Single, large, nearly rounded, orange red-colored flowers. Freely and continuously flowering; usually about 8 to 9 flowers and flower buds per lateral branch. Flowers positioned above or beyond the foliage; flowers typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 9.5 weeks after planting.

*Flower buds.*—Length: About 2.2 cm. Diameter: About 1.6 cm. Shape: Ovoid. Color: 40A.

*Flower length.*—About 7.5 to 8 cm.

*Flower width.*—About 7.3 to 7.5 cm.

*Flower depth.*—About 1 cm.

*Petals.*—Quantity: Five per flower, imbricate. Length: Banner petals: About 2.8 to 3 cm. Lateral and base petals: About 3.5 to 4.2 cm. Width: Banner petal: About 4.8 to 5.2 cm. Lateral and base petals: About 3.2 to 4.2 cm. Shape: Cordate. Apex: Weakly lobed. Base: Attenuate. Margin: Entire. Aspect: Mostly flat. Texture: Smooth; satiny. Color: When opening, upper and lower surfaces: 40A. Fully opened, upper surface: 33A; small eye zone, 57C; color becoming closer to 43C with development. Fully opened, lower surface: 40A.

*Spur.*—Quantity: One per flower. Length: About 5.5 to 6.5 cm. Diameter: At apex: About 0.5 mm. At flower: About 3 mm. Aspect: Curved. Color: 53D.

*Peduncles.*—Length: About 4.5 to 5 cm. Diameter: About 2 mm. Texture: Smooth, glabrous. Strength: Strong, flexible. Color: 179B.

*Reproductive organs.*—Androecium: Stamen number: Five fused at anthers, hooded; filaments free. Anther length: About 5 to 6 mm. Anther shape: Obovate. Anther color: 46C. Pollen amount: Moderate. Pollen color: 8D. Gynoecium: Pistil quantity: One per flower. Pistil length: About 6 to 7 mm. Stigma color: 46C. Style color: 46C. Ovary: Five-celled. Ovary color: 139A.

*Seed/fruit.*—Seed and fruit development has not been observed.

Disease/pest resistance: Plants of the new Impatiens have not been observed to be resistant to pathogens and pests common to Impatiens.

Low temperature tolerance: Plants of the new Impatiens have been observed to tolerate night temperatures of 5° C. with 10° C. day temperatures.

It is claimed:

1. A new and distinct cultivar of New Guinea Impatiens plant named 'Fisupnic Salmon', as illustrated and described.

* * * * *

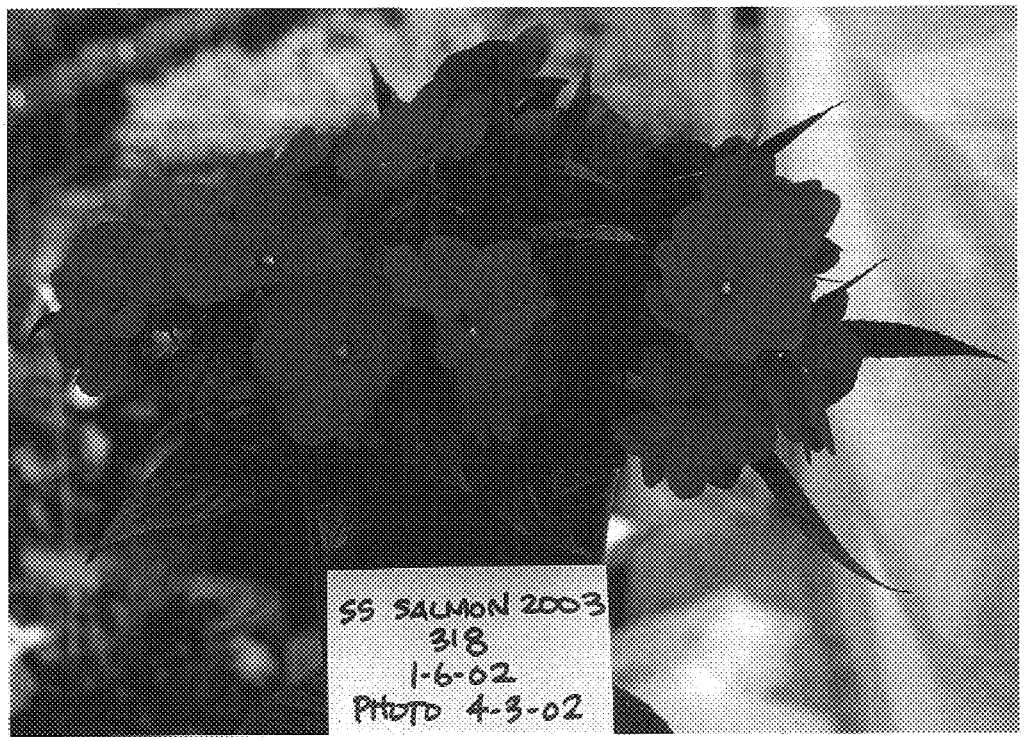
SS SALMON 2003
318
1-6-02
PHOTO 4-3-02